(12) United States Patent
Ferreira

(10) Patent No.: US 8,323,284 B2
(45) Date of Patent: Dec. 4, 2012

(54) ADAPTER DRIVER FOR ORTHOPAEDIC REAMER

(75) Inventor: Julian Ferreira, Tewkesbury (GB)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 427 days.

(21) Appl. No.: 12/237,057

(22) Filed: Sep. 24, 2008

(65) Prior Publication Data

US 2009/0082772 A1 Mar. 26, 2009

Related U.S. Application Data

(60) Provisional application No. 60/974,605, filed on Sep. 24, 2007.

(51) Int. Cl.
*A61B 17/00* (2006.01)

(52) U.S. Cl. ............ 606/80; 606/81; 606/86 R; 606/91; 606/96; 606/99

(58) Field of Classification Search .................... 606/80, 606/81, 84, 91, 86 R–89, 96–98
See application file for complete search history.

(56) References Cited

U.S. PATENT DOCUMENTS

| | | | |
|---|---|---|---|
| 3,702,611 A | 11/1972 | Fishbein | |
| 5,540,697 A * | 7/1996 | Rehmann et al. | 606/91 |
| 5,553,675 A | 9/1996 | Pitzen et al. | |
| 5,658,290 A * | 8/1997 | Lechot | 606/80 |
| 5,817,096 A | 10/1998 | Salyer | |
| 5,980,170 A * | 11/1999 | Salyer | 408/239 R |
| 6,126,359 A * | 10/2000 | Dittrich et al. | 403/349 |
| 6,258,107 B1 | 7/2001 | Balazs et al. | |
| 6,283,972 B1 | 9/2001 | Riley | |
| 6,854,742 B2 | 2/2005 | Salyer et al. | |
| 7,115,119 B2 | 10/2006 | Desarzens | |
| 7,229,078 B2 | 6/2007 | Lechot | |
| 7,326,198 B2 | 2/2008 | Desarzens et al. | |
| 2002/0099380 A1* | 7/2002 | Salyer et al. | 606/80 |
| 2003/0216716 A1* | 11/2003 | Desarzens | 606/1 |
| 2004/0049199 A1* | 3/2004 | Lechot et al. | 606/80 |

* cited by examiner

*Primary Examiner* — Kevin T Truong
*Assistant Examiner* — Samuel Hanna
(74) *Attorney, Agent, or Firm* — Taylor IP, P.C.

(57) ABSTRACT

An adapter for a crossbar surgical reamer having a base with an interface for connecting with another style of reamer such as a crossbar reamer. Intersecting axially facing recesses are provided on the end of the base for connection with a crossbar type of reamer. A pair of grips are pivotally mounted on the base and urged to a closed position by a cross spring to releasably hold the crossbar reamer within the recesses for installation and removal substantially in an axial direction.

2 Claims, 5 Drawing Sheets

ADAPTER DRIVER FOR ORTHOPAEDIC REAMER

CROSS REFERENCE TO RELATED APPLICATIONS

This is a non-provisional application based upon U.S. provisional patent application Ser. No. 60/974,605, entitled "DUAL ADAPTER DRIVER FOR ORTHOPAEDIC REAMER", filed Sep. 24, 2007, which is incorporated herein by reference.

BACKGROUND OF THE INVENTION

Field of the Invention

The present invention relates to orthopedic surgical reamers and more specifically to drivers for such tools.

In the field of orthopaedic surgery, it is often necessary to remove bone material to enable implantation of prosthesis to repair joints in the human body. Patella cutters and acetabular reamer cups and glenoid reamers are surgical tools which are used in surgery for the insertion of artificial joints. Acetabular reamer cups are used to cut hemispherical cavities in pelvis bones for the insertion of artificial hip joints. Patella cutters are used to shape the underside of the patella or knee cap during knee replacement surgery. Glenoid reamers are used to cut hemispherical cavities in shoulder bones for the insertion of artificial shoulder joints. Patella cutters have a complex arrangement of precisely shaped cutting edges arranged around an axis of rotation for cutting the patella. Acetabular reamer cups and glenoid reamers have a complex arrangement of cutting edges arranged on a spherical surface around the axis of rotation of the cup.

A number of tools have been developed for this purpose and include reamers having generally semi-hemispherical configuration with cutting elements on them so that a corresponding semi-hemispherical hollow can be formed in the bone material for providing a foundation for the repair of the joint.

There are two major driver styles in the field, one of which is for the Othy style manufactured by Symmetry Medical, Inc. and the other style manufactured by Precimed SA of L'Echelette, Switzerland. Although these both have semi-hemispherical cutting heads, they have different interfaces between driving tools with which they are associated. The Othy style has a crossbridge element. This element is a bar extending between the circumference of the hemisphere and having a circular expanded section in the middle. Numerous arrangements are available for securing this device as exemplified by U.S. Pat. No. 6,854,742. Alternatively, the Precimed reamer has a crossbar shape in which two circular cross section bars intersect at the center and extend to the walls of the hemisphere. An example of a driver for this type is found in U.S. Pat. No. 5,658,290 in which a bayonet interconnection is provided between the reamer and the driver.

Typically, surgeons use specialized drivers for each of the reamers. The drivers connect to a source of power and have appropriate handles for guiding the operation of the reamer by a surgeon. If a surgeon has one of the adaptors, it is difficult to utilize the other type of reamer since it requires a specialized driver for that reamer. It has been proposed in U.S. Pat. No. 7,115,119 to provide a dual adapter that accommodates both the Othy and the Precimed reamers. However, this style of dual reamer requires a bayonet interconnection in which the assemblies are inserted axially and then a rotational movement, in accordance with a bayonet connection, is provided to lock the elements in place. This type of action slows the process of utilizing a new reamer because of the additional movement, But, more than that, the release of the device, after it has been in the surgical environment, is more difficult because it requires holding the reamer to reverse the rotational movement and then axial movement to finally free the reamer.

What is needed in the art, therefore, is an adapter for surgical reamers that enables rapid and immediate connection and disconnection of the reamers.

SUMMARY OF THE INVENTION

In one form, the invention is an adaptor for a crossbar surgical reamer. The adapter has a base having intersecting axially facing recesses on one end thereof for receiving a crossbar style reamer. The base has an interface on the opposite end of the base for connection with a predetermined style of non-crossbar reamer driver. A pair of grips is mounted on the base for releasably holding a crossbar reamer in the grooves, wherein the crossbar reamer is installed and removed in an axial direction.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate embodiments of the invention, in one form, and such exemplifications are not to be construed as limiting the scope of the invention in any manner.

DETAILED DESCRIPTION OF THE INVENTION

Figure 1:
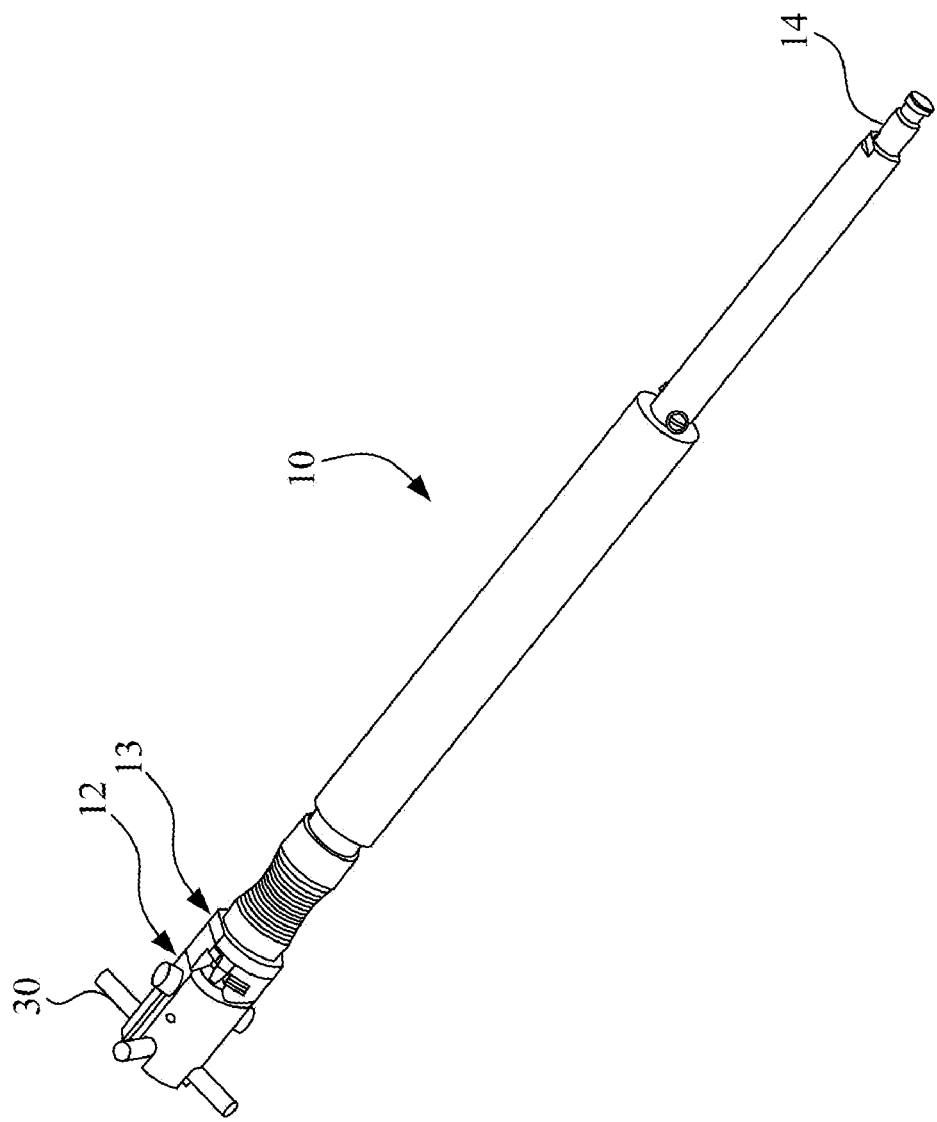
FIG. 1 shows a perspective view of a driver assembly, together with an adapter for a crossbar style reamer.

Referring to FIG. 1 there is shown a reamer driver assembly 10 having a proximal end 14 adapted to connect with a source of rotational power to cause the driver 10 to rotate. The driver 10 may be of the configuration shown in U.S. Pat. No. 6,854,742, of common assignment and the disclosure of which is herein incorporated in its entirety by reference. The driver 10 described above is specifically adapted to connect and disconnect with the Othy style of reamer which has a reamer interface consisting of a central circular section and tabs or projections radially extending from the center section. FIG. 1 shows the adapter 12 in place at the distal end 13 of reamer driver 10.

Figure 2:
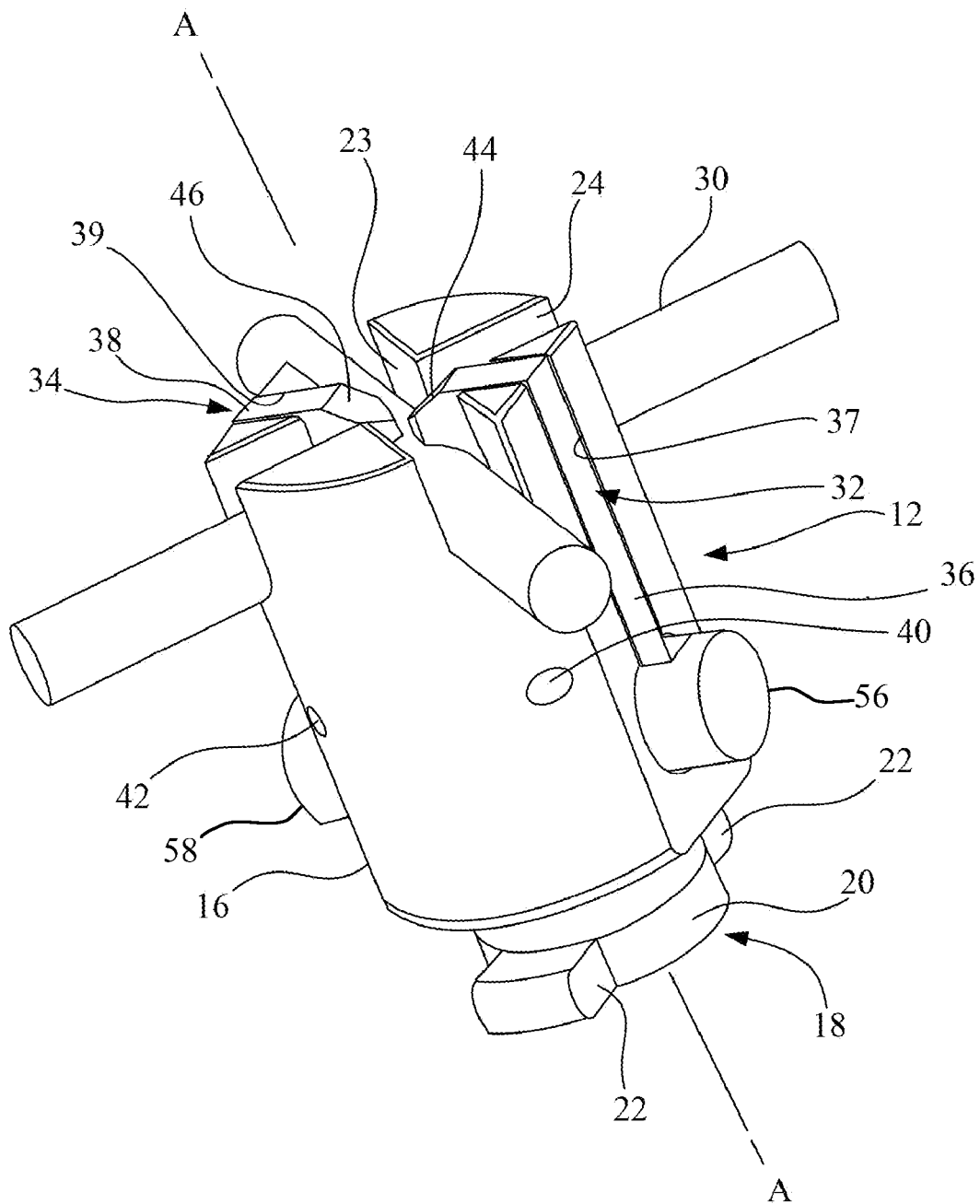
FIG. 2 is an enlarged perspective view of the adapter shown in FIG. 1.
Figure 3:
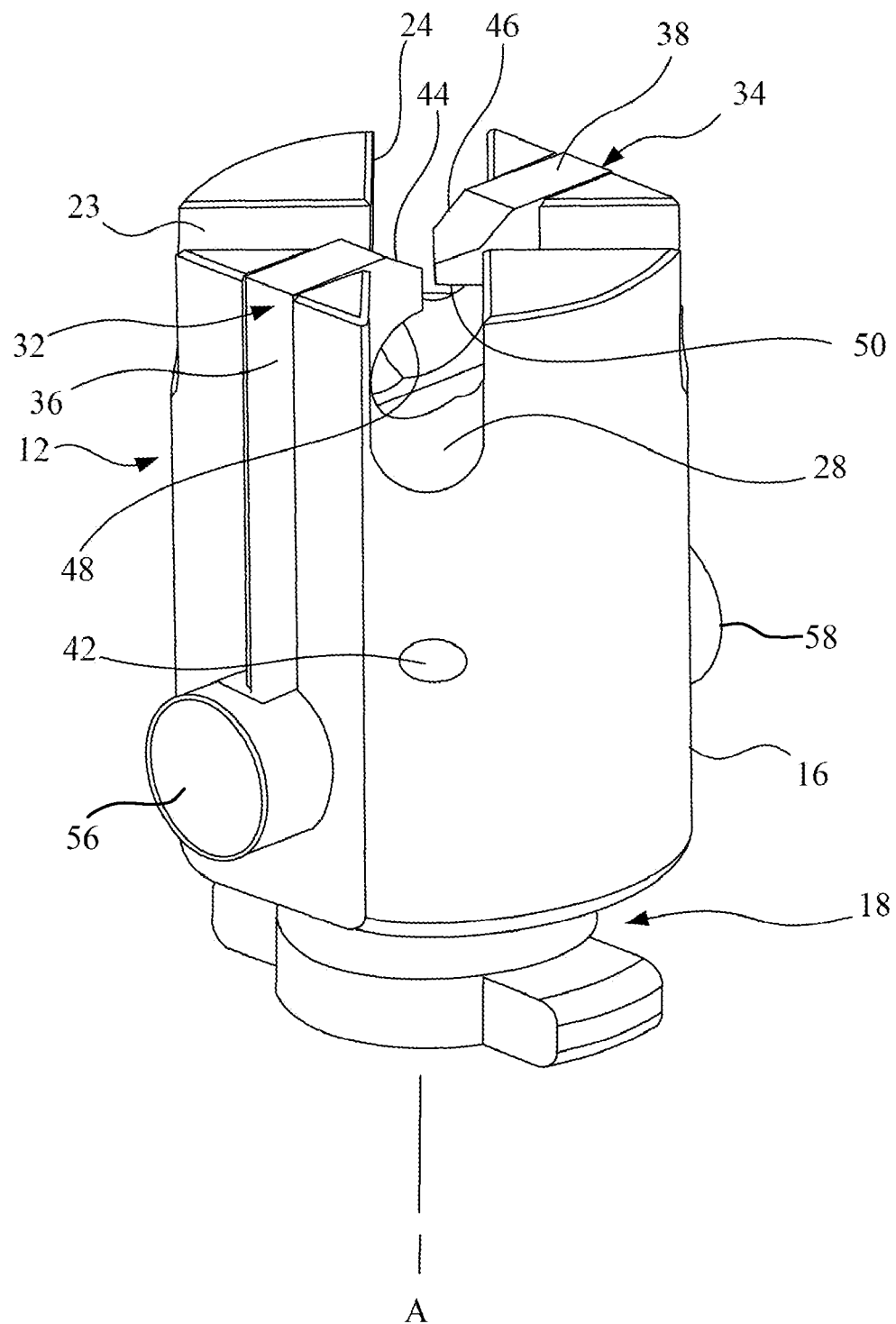
FIG. 3 shows a perspective view of the adapter of FIGS. 1 and 2 without a reamer but with the means for holding the reamer in a locked position.
Figure 4:
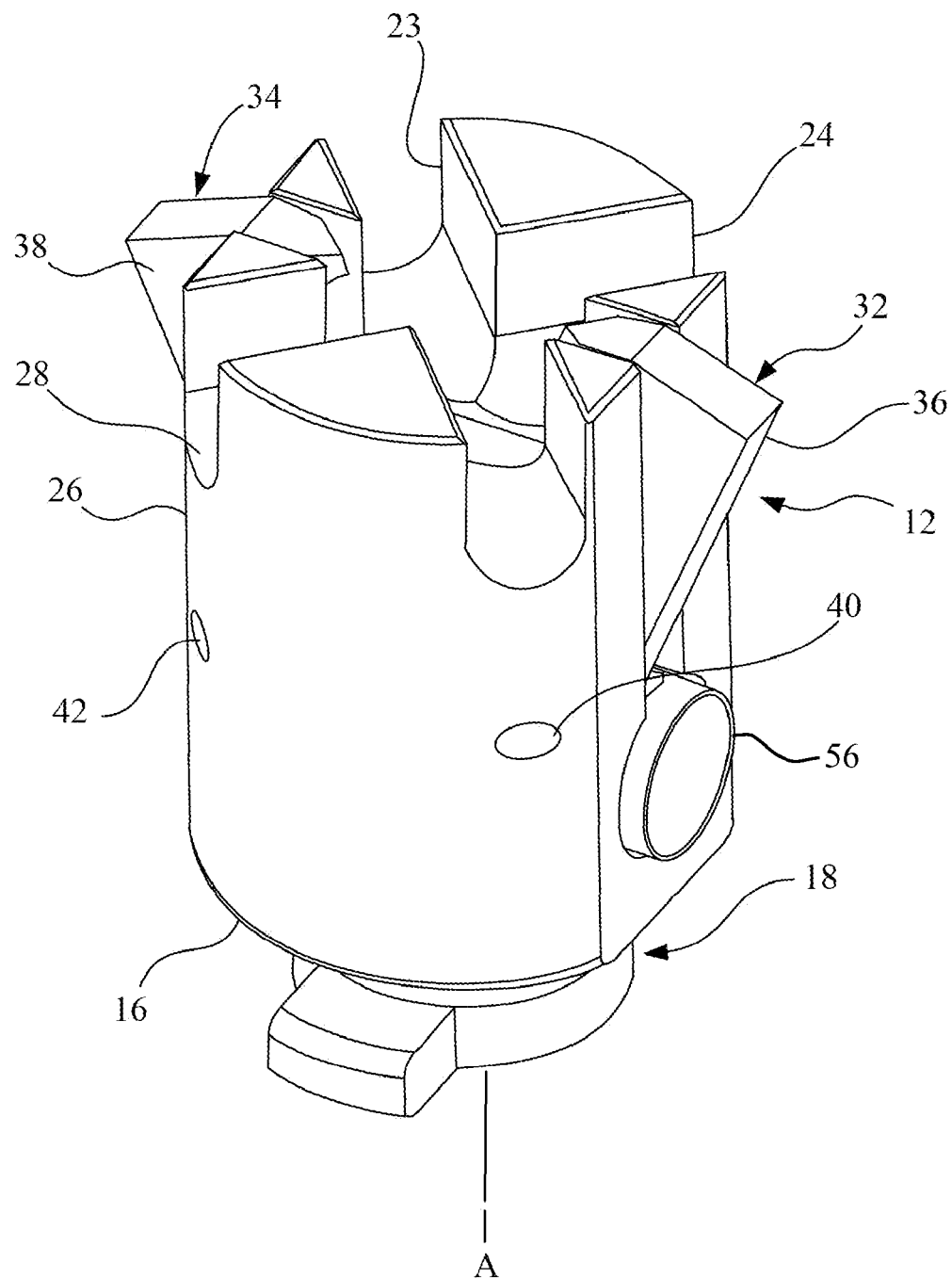
FIG. 4 shows the reamer adapter of FIGS. 1, 2, and 3 without the reamer but with the holding means in a position for permitting removal.

As shown particularly in FIG. 2, adapter 12 has a base 16 which has an integral interface 18 for adapting to the Othy crossbridge type of driver. As such, the adapter 18 has a circular center section 20 and a pair of radially extending tabs 22 for connection with the driver 10. As herein shown, the adapter section 18 is integral with base 16. However, it should be apparent to those skilled in the art that it can be fabricated from multiple components. As shown in FIGS. 2-4, base 16 has intersecting recesses 23 and 24 extending radially from a central axis A of adapter 12 and at substantially right angles with respect to each other. Each of the recesses 23 and 24 have a semicircular floor 26 and 28, respectively so as to receive a reamer of the crossbar type. It should be noted particularly with respect to FIG. 4 that the recesses 23 and 24 open to an axial direction so that a crossbar reamer interface 30, particularly shown in FIGS. 1 and 2 may be installed and removed substantially in an axial direction. The interface 30 includes a pair of rods crossing one another at central axis A and extending to the interior surface of a semi-hemispherical cutting head which is not shown to simplify an understanding of the present invention.

A pair of grips 32 and 34 is mounted on base 16 so as to releasably hold the crossbar reamer 30 in place in the recesses 23 and 24. As shown particularly in FIG. 5, the grips 32 and 34 comprise plates 36 and 38 pivotally mounted to base 16 in radial slots 37, 39 by pins 40 and 42, respectively. Plates 36 and 38 have end-wise projections 44 and 46 which are contoured to capture reamer 30 at curved surfaces 48 and 50, respectively when the plates 36 and 38 are in the illustrated position in FIGS. 2, 3 and 5.

Figure 5:
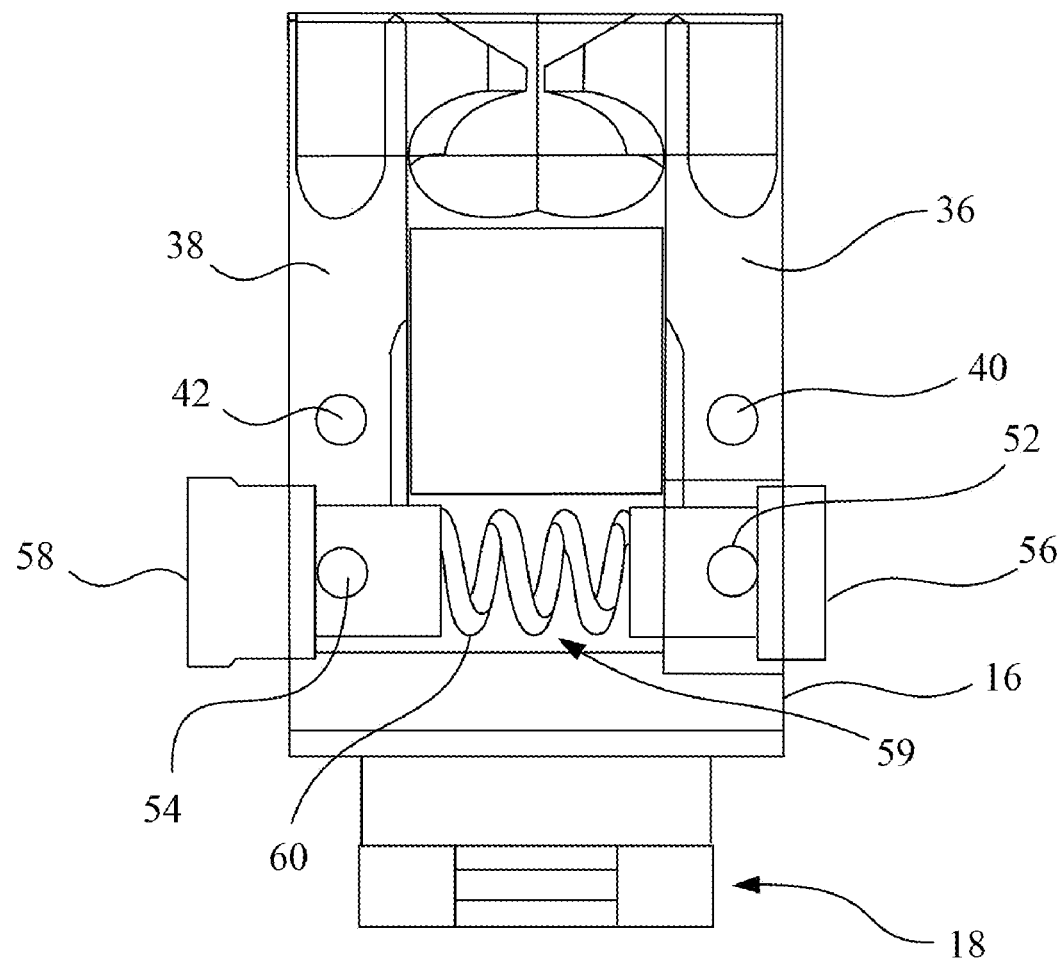
FIG. 5 is a cross section view of the adapter of FIGS. 1-4 taken on Lines 5-5 of FIG. 1.

As shown particularly in FIG. 5, the plates 36 and 38 have a lower pin connection 52 and 54 for pivotal mounting with a pair of plugs 56 and 58 respectively. The plugs are received within an appropriate radially extending bore 59 in base 16 and are urged radially outward by a cross spring 60. In the absence of radial pressure on plugs 56 and 58, the spring 60 urges the grips 32 and 34 into their position shown in FIGS. 2, 3 and 5. Inward pressure on plugs 56 and 58 by an operator causes them to be urged radially inward thus pivoting the projections 44 and 46 sufficiently to clear the recesses 23 and 24 and permit removal of the crossbar reamers 30 substantially in an axial direction.

The result of such an arrangement is a substantially simplified connection and release of the crossbar reamer 30, unlike prior systems requiring a bayonet connection in which removal is in an axial direction followed by rotational movement with removal being the reverse. Such an arrangement offers more rapid connection to the surgical reamer but, more importantly, allows simplified removal without the need to hold the reamer to permit the rotational movement.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An adapter for a crossbar surgical reamer comprising:
   a base having intersecting axially facing recesses at right angles with respect to one another and having semicircular floors on one end for receiving a pair of rods extending at a right angle with respect to one another (crossbar) style reamer;
   an interface having a center circular section and opposed radially extending tabs on the opposite end of said base for connection with a crossbridge style reamer driver;
   a pair of grips pivotaly mounted on said base for releasably holding a crossbar reamer in said recesses, wherein said grips have opposed projections on a far end with an inner concave surface for capturing and releasing said crossbar reamer, wherein said crossbar reamer is installed and removed in an axial direction and wherein said grips are pivotally mounted on said base for releasably holding said crossbar reamer;
   a radially extending bore in said base;
   a cross spring having opposed ends being received in said radially extending bore and being positioned horizontally in between a pair of opposed radial plugs so as to urge said plugs radially outward;
   said plugs being pivotally mounted to said grips at an opposite end to the far end of said grips for displacing said grips between the position of holding and releasing said crossbar reamer.

2. The adapter as claimed in claim 1, wherein said grips are pivotally mounted to said base at a location between the far end of the grips having the projections and the opposite end of said grips and said spring is positioned at the opposite end of said grips.

* * * * *